US010822296B2

(12) United States Patent
Shimamura et al.

(10) Patent No.: US 10,822,296 B2
(45) Date of Patent: *Nov. 3, 2020

(54) SODIUM DIACETATE CRYSTAL AND SOLID DIALYSIS PREPARATION COMPRISING SAID CRYSTAL

(71) Applicant: FUSO PHARMACEUTICAL INDUSTRIES, LTD., Osaka-shi, Osaka (JP)

(72) Inventors: Hideo Shimamura, Osaka (JP); Tadataka Murakami, Suita (JP); Yasunori Kurata, Osaka (JP); Ayaka Kato, Osaka (JP)

(73) Assignee: FUSO PHARMACEUTICAL INDUSTRIES, LTD., Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/728,102

(22) Filed: Oct. 9, 2017

(65) Prior Publication Data

US 2018/0362438 A1 Dec. 20, 2018

Related U.S. Application Data

(63) Continuation of application No. 15/034,828, filed as application No. PCT/JP2014/079992 on Nov. 12, 2014, now Pat. No. 9,840,452.

(30) Foreign Application Priority Data

Nov. 12, 2013 (JP) .................. 2013-234114

(51) Int. Cl.
*C07C 53/10* (2006.01)
*C07C 51/02* (2006.01)
(Continued)

(52) U.S. Cl.
CPC ............ *C07C 53/10* (2013.01); *A61K 9/1605* (2013.01); *A61K 9/1617* (2013.01);
(Continued)

(58) Field of Classification Search
None
See application file for complete search history.

(56) References Cited

U.S. PATENT DOCUMENTS 5,540,842 A 7/1996 Aoyama et al.
9,840,452 B2 * 12/2017 Shimamura ............. C07C 53/10
(Continued)

FOREIGN PATENT DOCUMENTS

CN 1448145 A 10/2003
JP 6-178802 A 6/1994
(Continued)

OTHER PUBLICATIONS

Chen ("Progress in synthesis of sodium diacetate for mildew preventive agent" Food Science and Technology, vol. 35, No. 5, 2010, p. 277-280, of record of the IDS filed on Oct. 9, 2017, including English language translation thereof) (Year: 2010).*

(Continued)

*Primary Examiner* — Amy C Bonaparte
(74) *Attorney, Agent, or Firm* — Hamre, Schumann, Mueller & Larson, P.C.

(57) ABSTRACT

A novel highly stable sodium diacetate crystal, in which the volatilization of acetic acid can be suppressed for a long period. More specifically, a sodium diacetate crystal having a median diameter in the range of 300 to 3000 μm.

4 Claims, 6 Drawing Sheets

(51) Int. Cl.

| | |
|---|---|
| C07C 51/41 | (2006.01) |
| A61K 9/16 | (2006.01) |
| A61K 45/06 | (2006.01) |
| A61P 7/08 | (2006.01) |
| A61K 33/20 | (2006.01) |
| A61M 1/16 | (2006.01) |
| C07C 51/347 | (2006.01) |

(52) U.S. Cl.
CPC ............ *A61K 9/1623* (2013.01); *A61K 33/20* (2013.01); *A61K 45/06* (2013.01); *A61M 1/1654* (2013.01); *A61P 7/08* (2018.01); *C07C 51/02* (2013.01); *C07C 51/347* (2013.01); *C07C 51/41* (2013.01); *C07C 51/412* (2013.01)

(56) References Cited

U.S. PATENT DOCUMENTS

| | | | |
|---|---|---|---|
| 2014/0037710 A1† | 2/2014 | Hashimoto | |
| 2014/0046276 A1 | 2/2014 | Bjarnsholt et al. | |
| 2014/0097386 A1* | 4/2014 | Noguchi | A61K 31/7004 252/364 |
| 2015/0164862 A1 | 6/2015 | Suzuki et al. | |

FOREIGN PATENT DOCUMENTS

| | | | |
|---|---|---|---|
| JP | H0759846 | * | 3/1995 |
| JP | 10-259133 A | | 9/1998 |
| JP | 11-114054 A | | 4/1999 |
| JP | 2000-26280 A | | 1/2000 |
| JP | 2003-144115 A | | 5/2003 |
| JP | 3433979 B1 | | 8/2003 |
| JP | 3433979 B2 † | | 8/2003 |
| JP | 2005-230361 A | | 9/2005 |
| JP | 3693889 B2 | | 9/2005 |
| JP | 2007-131563 A | | 5/2007 |
| JP | 4001062 B2 | | 10/2007 |
| JP | 2008-23146 A | | 2/2008 |
| JP | 4299752 B2 | | 7/2009 |
| JP | 4370729 B2 | | 11/2009 |
| JP | 4878233 B2 | | 2/2012 |
| JP | 5376480 B1 | | 12/2013 |
| JP | 5517321 B1 | | 6/2014 |
| JP | 5517322 B1 | | 6/2014 |
| WO | 2012/143013 A1 † | | 10/2012 |
| WO | 2012/144405 A1 | | 10/2012 |
| WO | 2012144405 A1 † | | 10/2012 |
| WO | 2015/050188 A1 | | 4/2015 |
| WO | 2015-050189 A1 | | 4/2015 |

OTHER PUBLICATIONS

Dissolve. (1992). In C. G. Morris (Ed.), Academic Press Dictionary of Science and Technology (4th ed.). Oxford, UK: Elsevier Science & Technology. Retrieved from https://search.credoreference.com/content/entry/apdst/dissolve/0?institutionId=743 (Year: 1992).*
Solution. (1992). In C. G. Morris (Ed.), Academic Press Dictionary of Science and Technology (4th ed.). Oxford, UK: Elsevier Science & Technology. Retrieved from https://search.credoreference.com/content/entry/apdst/solution/0?institutionId=743 (Year: 1992).*
MIT ("Growing Quality Crystals", downloaded from https://web.archive.org/web/20050211084238/https://web.mit.edu/x-ray/cystallize.html, on Mar. 4, 2019, available online since at least Feb. 11, 2005) (Year: 2005).*
Chen ("Progress in synthesis of sodium diacetate for mildew preventive agent" Food Science and Technology, vol. 35, No. 5, 2010, p. 277-280, of record in the IDS filed on Oct. 9, 2017, including English language translation thereof) (Year: 2010).*
Dissolve. (1992). In C. G. Morris (Ed.), Academic Press Dictionary of Science and Technology (4th ed.). Oxford, UK: Elsevier Science & Technology. Retrieved from https://search.credoreference.com/content/entry/apdst/dissolve/0?institutionId=743, downloaded on Mar. 4, 2019 (Year: 1992).*
Solution. (1992). In C. G. Morris (Ed.), Academic Press Dictionary of Science and Technology (4th ed.). Oxford, UK: Elsevier Science & Technology. Retrieved from https://search.credoreference.com/content/entry/apdst/solution/0?institutionId=743, downloaded on Mar. 4, 2019 (Year: 1992).*
English language translation of JP H0759846, dated Jun. 7, 2019 (Year: 2019).*
Stevens et al. Experimental Electron Density Distribution of Sodium Hydrogen Diacetate. Evidence for Covalency in a Short Hydrogen Bond, Journal of the American Chemical Society, vol. 99, No. 8, ppl. 2829-2831 (1977.
Barrow et al. Crystal Structures of Some Acid Salts of Monobasic Acids. Part XVII. Structure of Sodium Hydrogen Diacetate, redetermined by Neutron Diffraction, J.C.S Perkins II, pp. 15-18 (1975).
Ashizawa et al. A case of dialysis patient who show a prominent allergic reaction against a small amount of acetic acid in a bicarbonate dialysate, Journal of the Kyusyu Society for Dialysis Therapy, vol. 26, pp. 87 (1998), and English translation.
International Search Report, PCT/JP2014/079992, dated Feb. 3, 2015 (5 pages).
International Preliminary Report on Patentability and Written Opinion, and English translation, PCT/JP2014/079992, dated Feb. 3, 2015 (13 pages).
Shan ("Crystal structure of sodium diacetate" Jingxi Huagong, vol. 19, issue 7, 2002, p. 390-393) and full translation (p. 1-12).
Chen ("Progress in synthesis of sodium diacetate for mildew preventative agent") Shipin Keji, vol. 35, issue 5, p. 277-280, 2010) and partial translation (3 pages).
Shan ("Molecular formula of sodium diacetate" Jingxi Huagong, vol. 18, issue 4, 2001, p. 220-222).
Tang ("Sodium diacetate: preparation and applications" p. 23-26, 2001, vol. 21, issue 3).
The partial supplementary European search report of European Patent No. 14861241.9, dated Jun. 22, 2017, 15 pages provided.
Brittain ("Polymorphism in Pharmaceutical Solids", Harry G. Brittain, Ed., 1999, p. 235-237, section on X-Ray Powder Diffraction).
English language translation of Chen ("Progress in synthesis of sodium diacetate for mildew preventative agent") Shipin Keji, vol. 35, issue 5, p. 277-280, 2010).
Song ("Study on preparation of sodium diacetate in methanol" Journal of Hubei Institute for Nationalities (Nat.Sci.), vol. 19, No. 4, 2001, p. 57-59) and English language translation thereof.
Shang ("Study on synthesis of sodium diacetate from acetic acid and sodium acetate" Journal of Hubei University of Science and Technology, vol. 29, No. 4, 2008, p. 317-319) and English language translation thereof.
Xiaojun Tan and Dangsheng Wang, Synthesis method and application of sodium diacetate, vol. 10,2006, pp. 26-27.
Niacet Catalog: http://www.niacet.com/wp-content/uploads/Brochure-Niacet-Progusta-SD.pdf, Oct. 2013.
Crystal, McGraw-Hili Encyclopedia of Science and Technology, 11 th edition, pp. 100-101, 2012.
Handbook of Clays and Clay Minerals (3rd Ed., Apr. 30, 2009), The Clay Science Society of Japan; with English translation of the relevant portion.
Dictionary of Physical and Chemical Science (3rd Ed., Enlarged edition, 2 Oct. 20, 1981), Iwanami Shoten, Publishers; with English translation of the relevant portion.
Handbook for Instrumental Analysis (3), Jul. 10, 1986, Kagaku-Dojin Publishing Company, Inc.; with English translation of the relevant portion.
Basic Book in Ceramics 3 X-ray Diffraction Analysis, Apr. 20, 1990, Uchida Rokakuho Publishing Co. Ltd.; with English translation of the relevant portion.
The extended European Search Report of European application No. 14861241.9 dated Sep. 1, 2017.
Shan et al., "About molecular formular of Sodium diacetate", Jingxi Huagong (Fine Chemicals), vol. 18, No. 4, Apr. 2001, pp. 220-222, xp008184766, 3 pages, Jingxi Huagong Bianjibu, Dallian, CN ISSN; 1003-5214, including English abstract.

(56) References Cited

OTHER PUBLICATIONS

Progusta SD Sodium Diacetate, Oct. 2013, Niacet Catalog, http://www.niacet.com/wp-content/uploads/Brochure-Niacet-Progusta-SD.pdf.†
Xiaojun Tan, Dangsheng Wang, Synthesis method and application of sodium diacetate, pp. 26-27, vol. 10, 2006, China Feed.†
Amended Claims with Annotations of Application No. EP 14861241, pp. 46-49, Mar. 20, 2018, European Patent Office, http://register.epo.org/application?number=EP14861241&Ing=en&tab=doclist.†
Amended Claims with Annotations of Application No. EP 14861241, pp. 46-48, Sep. 11, 2018, European Patent Office, http://register.epo.org/application?number=EP14861241&Ing=en&tab=doclist.†
Supplementary European Search Report of Application No. EP 14861241, Sep. 1, 2017, European Patent Office, http://register.epo.org/application?number=EP14861241&Ing=en&tab=doclist.†
Russell English, Partial European Search Report of Application No. EP 14861241, Jun. 22, 2017, European Patent Office, http://register.epo.org/application?number=EP14861241&Ing=en&tab=doclist.†
Annex to Communication of Application No. EP 14861241, Jul. 4, 2018, European Patent Office, http://register.epo.org/application?number=EP14861241&Ing=en&tab=doclist.†
European Search Opinion of Application No. EP 14861241.9, dated Sep. 1, 2017, European Patent Office, http://register.epo.org/application?number=EP14861241&Ing=en&tab=doclist.†
Cheng-Ji Shan, Ze-xin Zhang, Ning-hai Hu, Heng-qing Jia, Yan Xiang, About the Molecular Formula of Sodium Diacetate, pp. 220-222, Apr. 2001, vol. 18, No. 4, Fine Chemicals.†
Provisional Opinion Accompanying the Partial Search Results of Application No. EP 14861241.9, Jun. 22, 2017, European Patent Office, http://register.epo.org/application?number=EP14861241&Ing=en&tab=doclist.†

\* cited by examiner
† cited by third party

[Fig. 3]
A
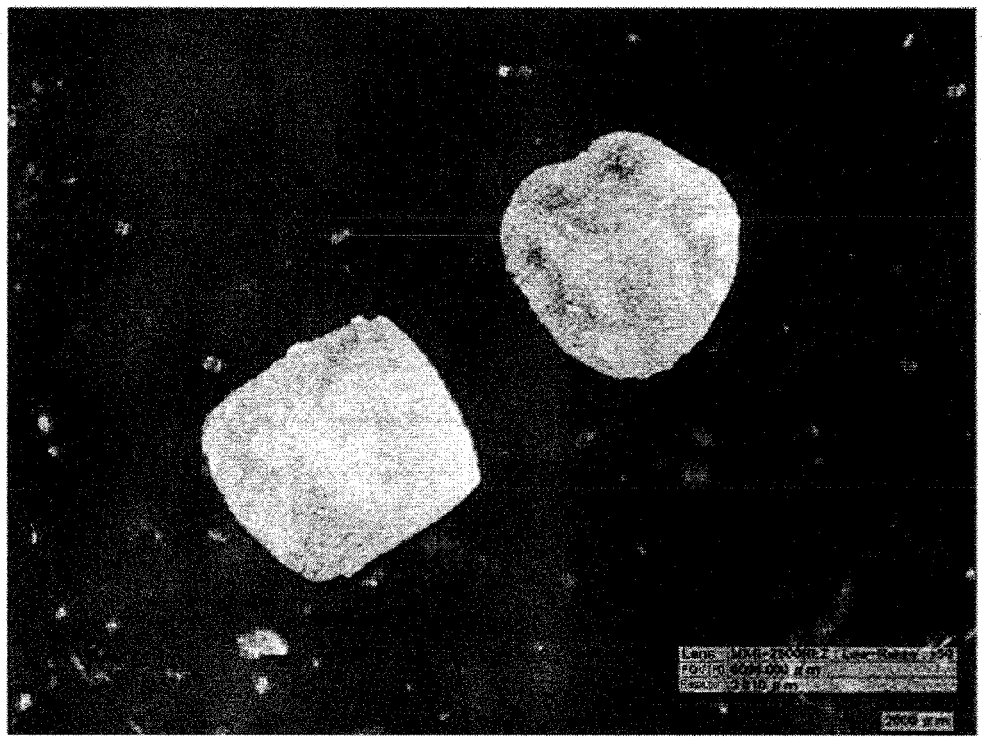
FOV (H)
B
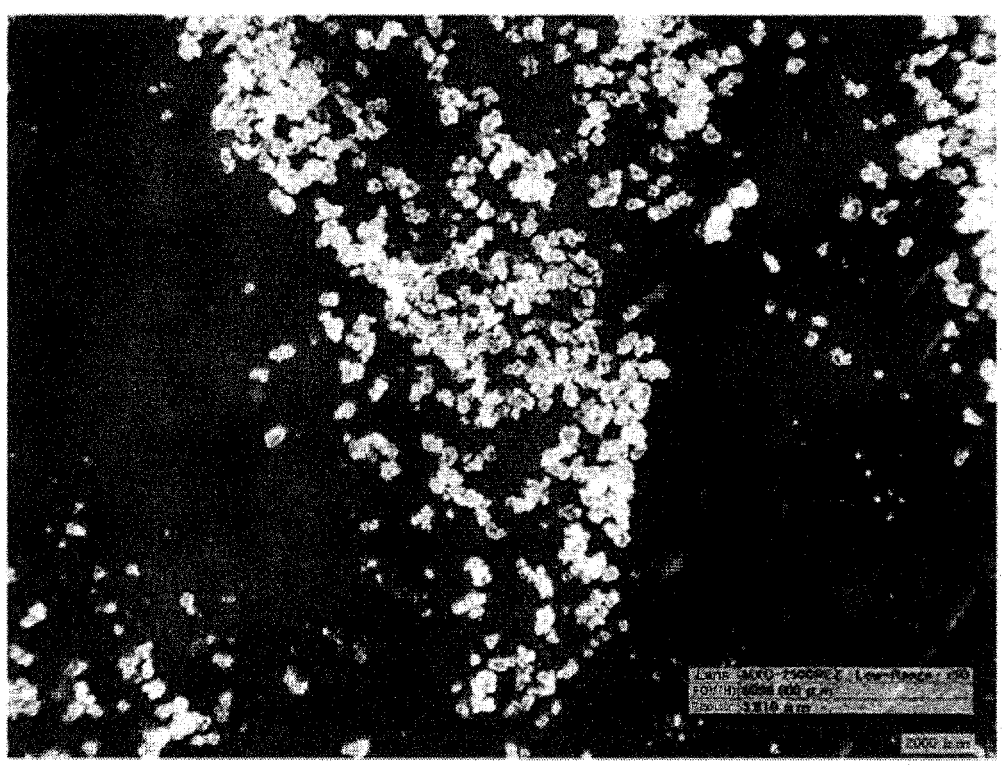

[Fig 4]
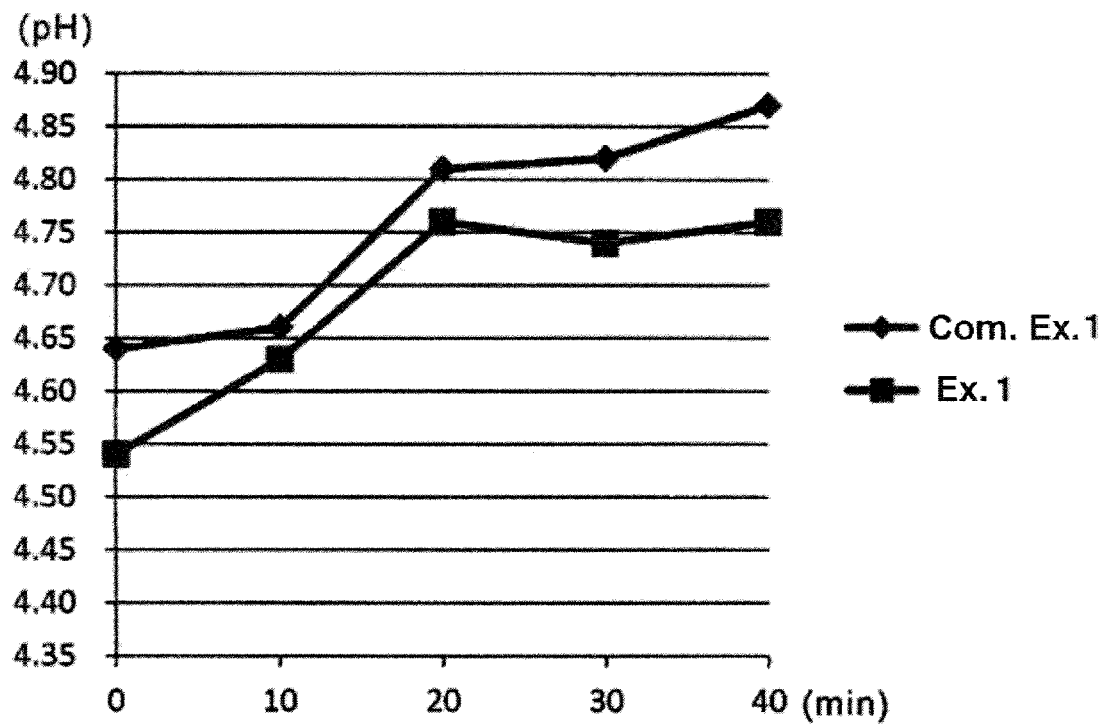
[Fig. 5]
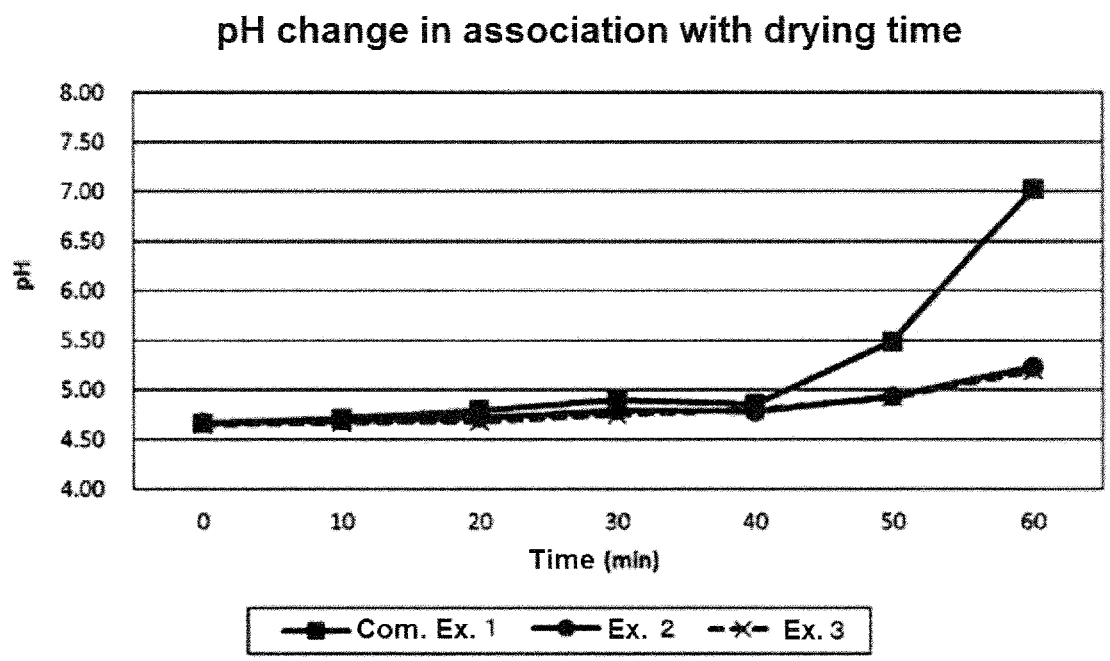

[Fig. 6]
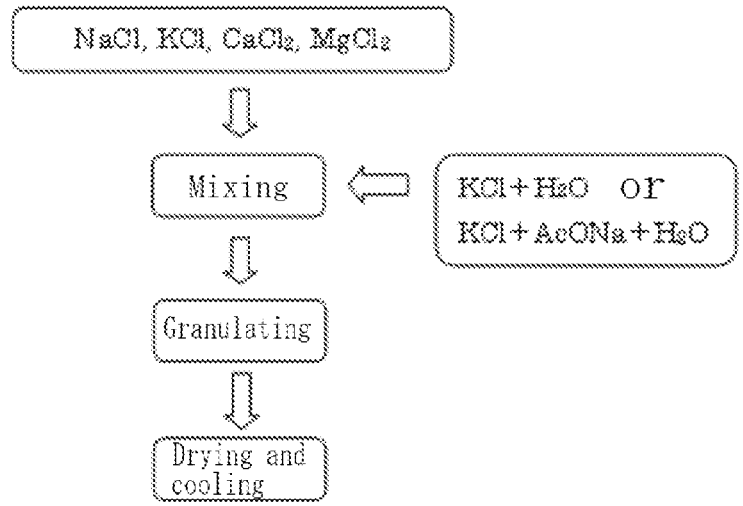
[Fig. 7]
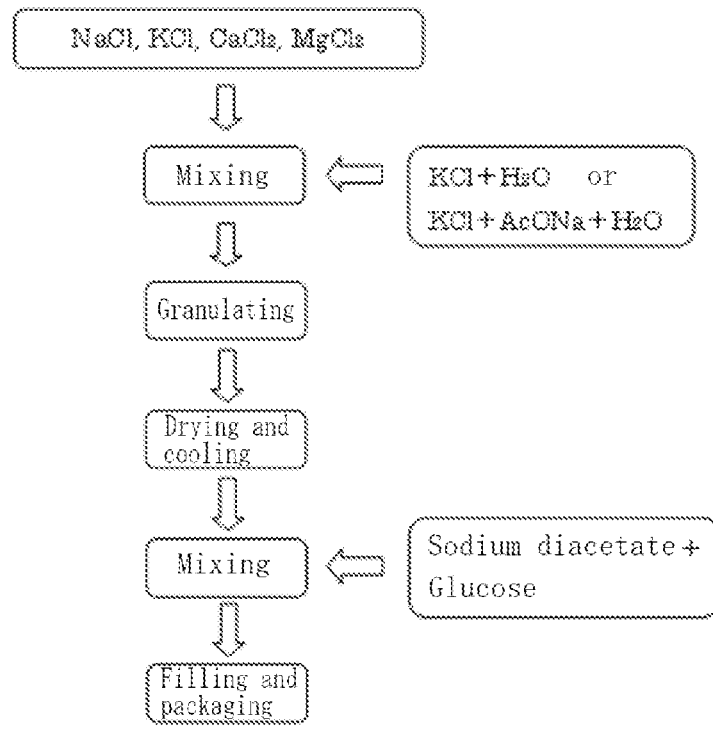

[Fig. 8]
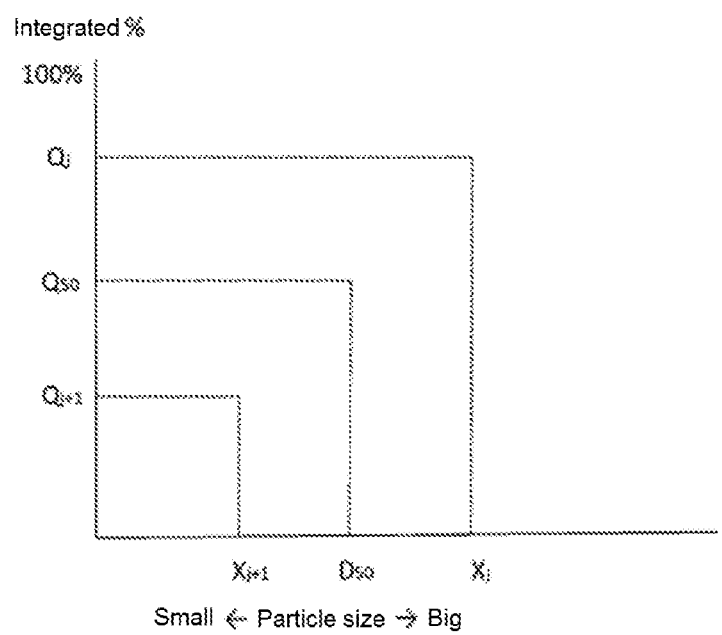

SODIUM DIACETATE CRYSTAL AND SOLID DIALYSIS PREPARATION COMPRISING SAID CRYSTAL

TECHNICAL FIELD

This application claims the priority to Japanese Patent Application No. 2013-234114, which is incorporated herein by reference in its entirety.

The present application relates to a novel sodium diacetate crystal, solid preparations or compositions for dialysis comprising said crystal (hereinafter correctly referred to as "the solid dialysis preparation"), and a method for the preparation thereof.

BACKGROUND ART

Sodium diacetate is a crystalline powder particle consisting of acetic acid and sodium acetate at the molar ratio of 1:1. In the field of foods, it is used as a food additive, such as an acidic ingredient (powdery acetic acid and Sushi Seasoning Mixes) or a pH adjuster, or a fungicide or a sequestering agent, or an adhesion preventing agent. In addition, in solid dialysis preparations for patients with renal failure, sodium diacetate is known to be incorporated for preventing the volatilization of a pH adjuster, acetic acid (Patent Literatures 1 to 3).

Sodium diacetate is mainly prepared by mixing of acetic acid and sodium carbonate or hydroxide (Non-patent Literature 1). Further, sodium diacetate may be prepared by spraying a mist of brewed vinegar to sodium acetate (Patent Literature 4).

The commercially available conventional sodium diacetates prepared as described above have smaller crystal size and lower stability to air and heat, and thus acetic acid is easily vaporized, leading to the generation of an acetic acid odor. Therefore, when it is used in dialysates, there is a problem that the an acetic acid odor is generated by the variation of pH, or by dissolving the dialysates in the manufacturing processes or in the medical settings, resulting in an obstacle for handling it.

On the other hand, in the field of foods, technologies for reducing the acetic acid odor by adding an agent such as maltitol, erythritol, and betaine for masking the odor have been proposed (Patent Literatures 5 and 6, etc.). However, such technologies were inappropriate for dialysates which are medicaments, because a huge amount of such additives is necessary for masking the odor.

Further, it has been suggested to aspirate the odor after the addition of acetic acid to granules during the preparation of dialysis preparations (Patent Literatures 7 and 8). However, it was not possible to suppress the volatilization of acetic acid with aging after the aspiration.

In dialysates, sodium bicarbonate is included to correct the acid-base balance of renal failure patients. In order to avoid a reaction of sodium bicarbonate with any other electrolyte components, the dialysates are generally prepared separately as an A agent (a formulation comprising calcium chloride and magnesium chloride, and so on without sodium bicarbonate) and a B agent (sodium bicarbonate), and they are mixed before use in order to use as dialysates. Previously, a liquid type agent was used as an A agent. Because of the massiveness and the inconvenient handling of the liquid, a solid dialysis preparation, which was solidified (powdered), has become prevalent. A known method for preparing an A agent for the solid dialysis preparation comprises using a suspension of potassium chloride, magnesium chloride and sodium acetate as a binder (binding agent) (Patent Literature 9). However, it was not possible to prepare an A agent exhibiting sufficient content uniformity by said method.

In addition, acetic acid at 8 to 12 mEq/L is predominantly used as a pH adjuster in a conventional dialysate, while said value is 80- to 120-times higher than the reference value in vivo. Since there is also an report that an increase of the blood concentration of acetic acid causes a significant allergic reaction (acetate intolerance) (Non-patent Literature 2), a dialysate with lower acetic acid concentration closer to a reference value, such as an acetic acid concentration below 5 mEq/L is needed. As for such dialysates, the low-acetate dialysates in which total acetate ion is not less than 2 mEq/L and less than 6 mEq/L have been developed (Patent Literatures 10 to 12).

Further, in case of the solid dialysis preparations using acetic acid, there is a report that the acetic acid odor is not generated when the molar ratio of acetic acid to sodium acetate in the formulations is from 1:3.6 to 4.3, while a strong acetic acid odor is generated if the ratio deviates from the range. (Patent Literature 13). However, when preparing a solid dialysis preparation with a low-acetate concentration, the pH is increased by adding the components in the amount covered by said ratio, and fine particles of calcium carbonate will occur when mixing with B agent. On the other hand, when preparing an A agent within the pH range which does not generate the fine particles, a strong acetic acid odor occurs, because the ratio of acetic acid to sodium acetate is 1:1, namely, beyond the above described range of the ratio.

CITATION LIST

Patent Literature

[Patent Literature 1] JP 3433979 B
[Patent Literature 2] JP 10-259133 A
[Patent Literature 3] JP 11-114054 A
[Patent Literature 4] JP 4299752 B
[Patent Literature 5] JP 2003-144115 A
[Patent Literature 6] JP 3693889 B
[Patent Literature 7] JP 4001062 B
[Patent Literature 8] JP 4370729 B
[Patent Literature 9] JP 4878233 B
[Patent Literature 10] JP 5376480 B
[Patent Literature 11] JP 5517321 B
[Patent Literature 12] JP 5517322 B
[Patent Literature 13] JP 2007-131563 A

Non-Patent Literature

[Non-patent Literature 1] J. C. S. Perkin 2. (1975)15-18.
[Non-patent Literature 2] Mamiko Ashizawa et al., Journal of the Kyusyu Society for Dialysis Therapy, 26, 87 (1998)

SUMMARY OF INVENTION

The problem to be solved by the present invention is to provide a novel sodium diacetate crystal having high stability, in which the volatilization of acetic acid can be suppressed for a long time, and a solid dialysis preparation, in which the volatilization of acetic acid and the decomposition of glucose can be suppressed, and thus an acetic acid odor can be reduced.

In addition, the problem to be solved by the present invention is to provide a method for preparing a solid dialysis preparation with superior content uniformity.

Means of Solving the Problems

In order to solve the problems described above, the present inventors have extensively studied to find that a sodium diacetate crystal with particular properties is high stable, in which the volatilization of acetic acid can be suppressed for a long time. Also, it has been found that the incorporation of said crystal, a particular production method, etc. make it possible to suppress the volatilization of acetic acid and to reduce an acetic acid odor and the decomposition of glucose, thereby providing a stable solid dialysis preparation and a low-acetate solid dialysis preparation with a reduced acetic acid odor. Furthermore, it has been found that the use of potassium chloride (and sodium acetate) suspension as a binder (binding agent) can provide a solid dialysis preparation with a superior content uniformity. And thus, the present invention has finally completed.

The present invention includes the followings:

[1] A crystal of sodium diacetate, which has a median size from 300 to 3000 μm.

[2] The crystal of above [1], which is a single crystal.

[3] A crystal of sodium diacetate, which has a powder X-ray diffraction pattern having a combination of peaks selected from 11.16, 13.65, 15.77, 19.33, 20.19, 20.90, 21.66, 22.38, 23.73, 25.04, 26.28, 27.47, 28.61, 29.80, 30.78, 31.82, 33.83, 34.76, 35.69, 36.60, 38.38, 39.22° (respectively ±0.2°) within the scanning range of the diffraction angle 2θ from 4.0 to 40.0°.

[4] A crystal of sodium diacetate, which has a powder X-ray diffraction pattern having a combination of peaks consisting of 11.16, 13.65, 15.77, 19.33, 20.19, 20.90, 21.66, 22.38, 23.73, 25.04, 26.28, 27.47, 28.61, 29.80, 30.78, 31.82, 33.83, 34.76, 35.69, 36.60, 38.38, 39.22° (respectively ±0.2°) within the scanning range of the diffraction angle 2θ from 4.0 to 40.0°.

[5] A crystal of sodium diacetate having a powder X-ray diffraction pattern as set forth in Table 1 below.

[6] A crystal of sodium diacetate having a powder X-ray diffraction pattern as depicted in FIG. 1.

[7] A crystal of sodium diacetate which can be prepared by a method comprising the steps of:
 (1) mixing acetic acid and sodium acetate in the molar ratio of from 1.5:1 to 1:2 (acetic acid:sodium acetate),
 (2) adding 0 to 2 wt % of water to the mixture, wherein said amount is based on the total weight of the mixture,
 (3) after the addition of water, heating the mixture to 130 to 250° C. to dissolve it, and
 (4) cooling the mixture, optionally with addition of a seed crystal after cooling.

[8] A method for preparing a crystal of sodium diacetate comprising the steps of:
 (1) mixing acetic acid and sodium acetate in the molar ratio of from 1.5:1 to 1:2 (acetic acid:sodium acetate),
 (2) adding 0 to 2 wt % of water to the mixture, wherein said amount is based on the total weight of the mixture,
 (3) after the addition of water, heating the mixture to 130 to 250° C. to dissolve it, and
 (4) cooling the mixture, optionally with addition of a seed crystal after cooling.

[9] A solid dialysis preparation comprising the crystal according to any one of above [1] to [7].

[10] A method for preparing a low acetate concentration solid dialysis preparation comprising the steps of:
 (1) preparing a mixture of sodium chloride, potassium chloride, calcium chloride and magnesium chloride,
 (2) adding a solution of potassium chloride and water or a solution or suspension of potassium chloride, sodium acetate and water to the mixture to granulate it, and
 (3) drying the resulting granules.

[11] A method for preparing a solid dialysis preparation comprising the steps of:
 (1) preparing a mixture of sodium chloride, potassium chloride, calcium chloride and magnesium chloride,
 (2) adding a solution of potassium chloride and water or a solution or suspension of potassium chloride, sodium acetate and water to the mixture to granulate it,
 (3) drying the resulting granules, and
 (4) adding glucose and sodium diacetate crystal to the granules to mix them.

[12] The method of [11], wherein the sodium diacetate crystal is the crystal of any one of above [1] to [7].

Effects of Invention

The sodium diacetate crystal of the present invention has high stability (for example, stability against heat or air), in which the volatilization of acetic acid can suppressed. Therefore, it is suitable for use as a food additive, a fungicide, a sequestering agent, an adhesion preventing agent, and a medicament such as a dialysate. For example, the incorporation of said crystal makes it possible to reduce the volatilization of acetic acid, thereby providing a solid dialysis preparation with a reduced acetic acid odor.

In addition, the method for preparing the crystal of the present invention can be used to easily adjust the size of the resulting crystal by changing the cooling period. Therefore, crystals having a size according to the intended use can be prepared.

The solid dialysis preparation of the present invention comprises said crystal, in which the volatilization of acetic acid is suppressed and thus an acetic acid odor is reduced. Therefore, a masking agent for reducing acetic acid odor is not needed for the solid dialysis preparation of the present invention. Further, when glucose is presented in the solid dialysis preparation, the decomposition of glucose by acetic acid can be suppressed, because the volatilization of acetic acid from the solid dialysis preparation is significantly suppressed compared to the commercially available conventional sodium diacetates. In addition, a low acetate concentration dialysate with a reduced acetic acid odor may also be prepared.

Furthermore, the use of a suspension of potassium chloride (and sodium acetate) as a binder (binding agent) in the method for preparing the solid dialysis preparation of the present invention makes it possible to prepare the dialysate with a superior content uniformity. In the method, the use of the crystal as defined above permits to suppress the volatilization of acetic acid and to reduce an acetic acid odor and the decomposition of glucose, thereby providing a stabilized solid dialysis preparation with a superior content uniformity.

BRIEF DESCRIPTION OF DRAWINGS

FIG. 3 Images of the crystal obtained in Example 1 (A) and the conventional crystal obtained in Comparative Example 1 (B) taken by using the digital microscope (HIROX Co., Ltd., "KH-7700").

FIG. 4 A graph comparing the stabilities of the crystal obtained in Example 1 with the conventional crystal obtained in Comparative Example 1 by measuring pH over time.

FIG. 5 A graph comparing the stabilities of the crystals obtained in Examples 2 and 3 with the conventional crystal obtained in Comparative Example 1 by measuring pH over time.

FIG. 6 A preparation flowchart for a solid dialysis preparation.

FIG. 7 A preparation flowchart for a solid dialysis preparation.

FIG. 8 A chart of particle size corresponding to the median of the particle size distribution.

DESCRIPTION OF EMBODIMENTS

The present invention provides the crystal which has a significantly larger crystal size compared to the conventional crystals. Namely, the crystal of the present invention has a crystal size within the range of generally from 300 to 3000 μm, and preferably from 500 to 2000 μm. As the crystal size becomes bigger, the specific surface area is getting smaller, and the volatilization of acetic acid is less likely to occur, thereby the stability to heat and air is improved.

The above described crystal size is intended to mean the size of each particle, not the size of an aggregate in which plural crystal particles are associated with each other.

The above crystal size is the "median size $(D_{50})$" measured in compliance with the mechanical agitation described in the analytical sieving method of the section of Particle Size Determination in the Japanese Pharmacopoeia as described below.

Preferably, the crystal of the present invention is a single crystal. As used herein, the "single crystal" is that a solid (a particle of crystal) is substantially consisting of a single crystal form, not a mixture of several crystalline polymorphs.

Preferably, the sodium diacetate crystal of the present invention has a powder X-ray diffraction pattern having a combination of peaks selected from 11.16, 13.65, 15.77, 19.33, 20.19, 20.90, 21.66, 22.38, 23.73, 25.04, 26.28, 27.47, 28.61, 29.80, 30.78, 31.82, 33.83, 34.76, 35.69, 36.60, 38.38, 39.22° (respectively ±0.2°) within the scanning range of the diffraction angle 2θ from 4.0 to 40.0°.

More preferably, the sodium diacetate crystal of the present invention has a powder X-ray diffraction pattern having a combination of peaks consisting of 11.16, 13.65, 15.77, 19.33, 20.19, 20.90, 21.66, 22.38, 23.73, 25.04, 26.28, 27.47, 28.61, 29.80, 30.78, 31.82, 33.83, 34.76, 35.69, 36.60, 38.38, 39.22° (respectively ±0.2°) within the scanning range of the diffraction angle 2θ from 4.0 to 40.0°.

Figure 1:
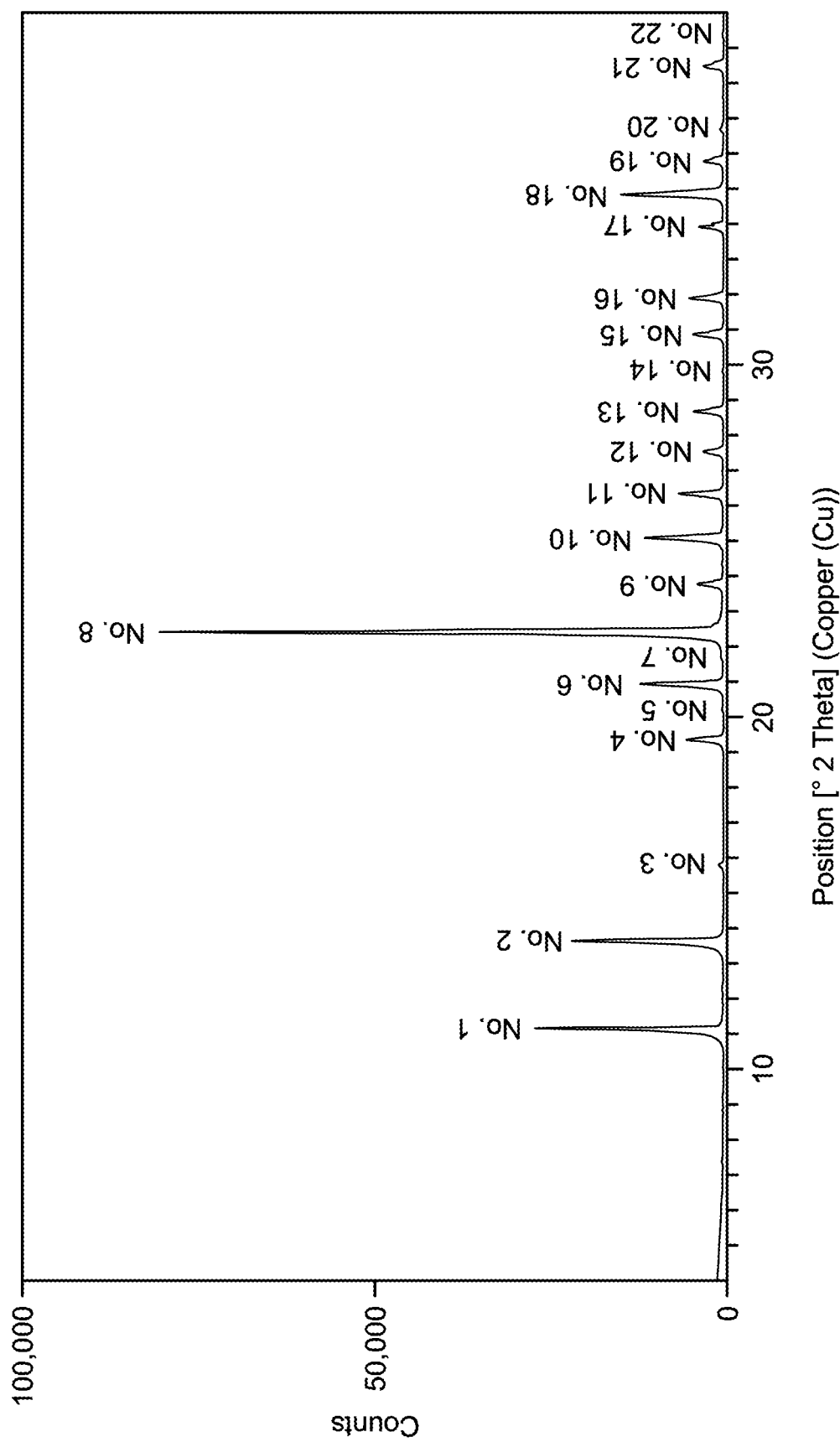
FIG. 1 A powder X-ray diffraction pattern of the crystal obtained in Example 1.

More preferably, the sodium diacetate crystal of the present invention has a powder X-ray diffraction pattern as set forth in Table 1 below or FIG. 1.

TABLE 1

| No. | Pos. [°2Th.] | d-spacing [Å] | NET intencity [cts] | Relative intensity [%] |
|---|---|---|---|---|
| 1 | 11.1605 | 7.92820 | 26758.21 | 33.09 |
| 2 | 13.6518 | 6.48649 | 20925.54 | 25.88 |
| 3 | 15.7738 | 5.61832 | 644.63 | 0.80 |
| 4 | 19.3315 | 4.59165 | 5340.13 | 6.60 |
| 5 | 20.1948 | 4.39727 | 274.54 | 0.34 |
| 6 | 20.8996 | 4.25054 | 12043.18 | 14.89 |
| 7 | 21.6592 | 4.10315 | 383.97 | 0.47 |

TABLE 1-continued

| No. | Pos. [°2Th.] | d-spacing [Å] | NET intencity [cts] | Relative intensity [%] |
|---|---|---|---|---|
| 8 | 22.3778 | 3.97300 | 80869.79 | 100.00 |
| 9 | 23.7331 | 3.74910 | 3783.16 | 4.68 |
| 10 | 25.0379 | 3.55659 | 11303.3 | 13.98 |
| 11 | 20.2780 | 3.39151 | 6553.25 | 8.10 |
| 12 | 27.4715 | 3.24682 | 3024.57 | 3.74 |
| 13 | 28.6062 | 3.12056 | 4242.16 | 5.25 |
| 14 | 29.8049 | 2.99772 | 93.49 | 0.12 |
| 15 | 30.7845 | 2.90453 | 4309.01 | 5.33 |
| 16 | 31.8208 | 2.81226 | 5006.29 | 6.19 |
| 17 | 33.8305 | 2.64747 | 3586.83 | 4.44 |
| 18 | 34.7557 | 2.57908 | 14622.64 | 18.08 |
| 19 | 35.6909 | 2.51362 | 2981.54 | 3.69 |
| 20 | 36.6025 | 2.45308 | 534.59 | 0.66 |
| 21 | 38.3763 | 2.34367 | 2938.49 | 3.63 |
| 22 | 39.2223 | 2.29505 | 182.52 | 0.23 |

The above powder X-ray diffraction patterns were obtained by measuring the following conditions.

[Measurement Condition]

X-ray diffractometer: X's Pert PRO MPD (Spectris Co., Ltd.)

Target: Cu

X-ray tube current: 40 mV

X-ray tube voltage: 45 kV

Scan range: 2θ=4.0-40.0°

Pretreatment: Grinding by using an agate mortar.

Figure 2:
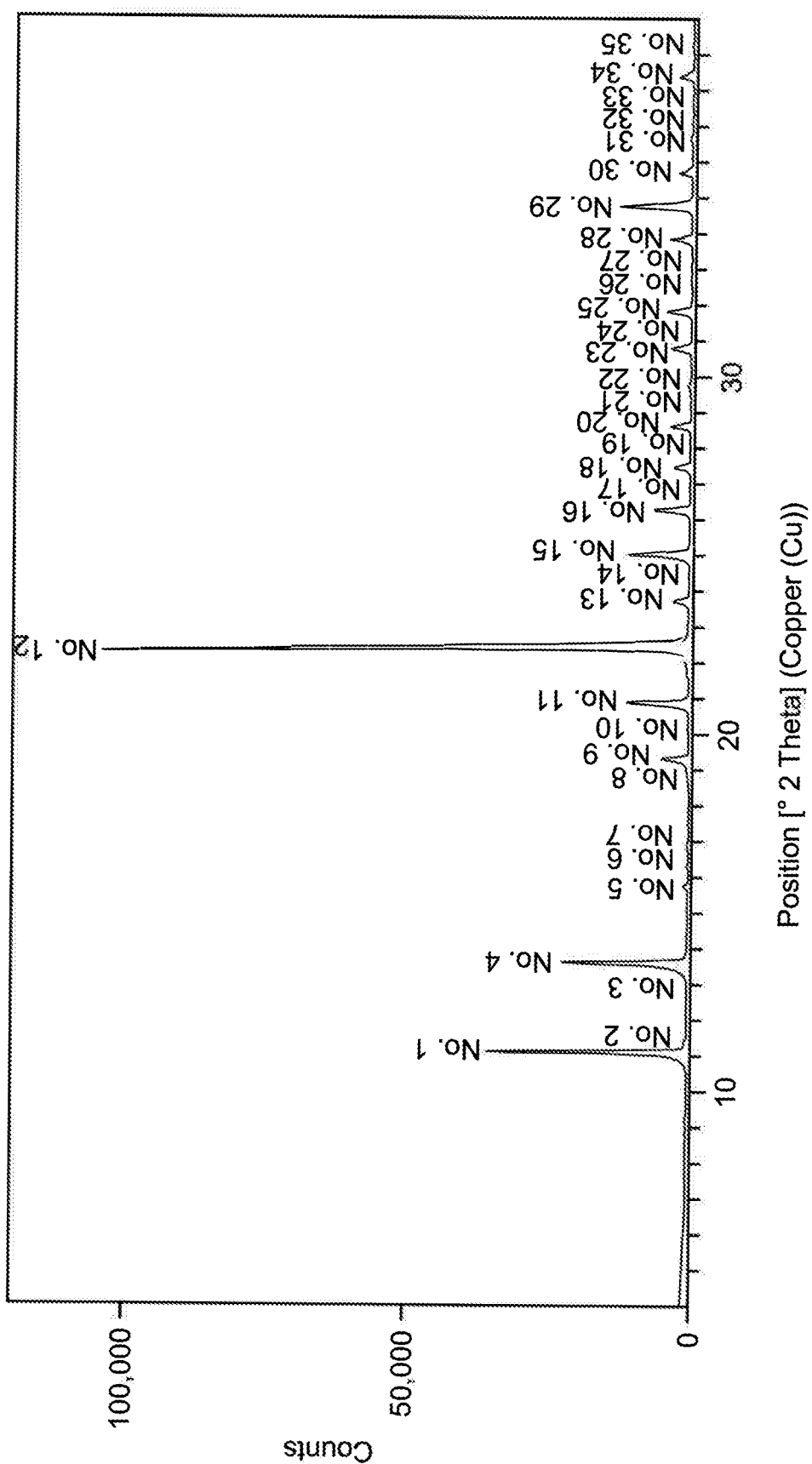
FIG. 2 A powder X-ray diffraction pattern of a conventional crystal obtained in Comparative Example 1.

The above-identified powder X-ray diffraction pattern is clearly different from that of the conventional crystal. As shown in Table 2 below or FIG. 2, the conventional crystal has many peaks which are missing in the crystal of the present invention, when measuring the powder X-ray diffraction pattern under the above described condition. It is believed that the difference is due to the fact that the crystal of the present invention is a single crystal, while the conventional crystal is a mixture of several crystalline polymorphs.

TABLE 2

| No. | Pos. [°2Th.] | d-spacing [Å] | NET intencity [cts] | Relative intensity [%] |
|---|---|---|---|---|
| 1 | 11.1363 | 7.94537 | 34815.76 | 32.95 |
| 2 | 11.4369 | 7.73718 | 565.73 | 0.54 |
| 3 | 12.7356 | 6.95097 | 121.36 | 0.11 |
| 4 | 13.6280 | 6.49777 | 21714.04 | 20.55 |
| 5 | 15.7429 | 5.62929 | 674.64 | 0.64 |
| 6 | 16.3453 | 5.42317 | 71.24 | 0.07 |
| 7 | 16.9426 | 5.23329 | 318.65 | 0.30 |
| 8 | 19.0191 | 4.66636 | 427.87 | 0.40 |
| 9 | 19.3112 | 4.59641 | 4957.96 | 4.69 |
| 10 | 20.1772 | 4.40105 | 337.24 | 0.32 |
| 11 | 20.8756 | 4.25537 | 11572.09 | 10.95 |
| 12 | 22.3550 | 3.97700 | 105659.40 | 100.00 |
| 13 | 23.7114 | 3.75248 | 3205.76 | 3.03 |
| 14 | 24.3667 | 3.65303 | 239.87 | 0.23 |
| 15 | 25.0118 | 3.56025 | 11152.42 | 10.56 |
| 16 | 26.2539 | 3.39456 | 6482.50 | 6.14 |
| 17 | 26.8610 | 3.31921 | 262.77 | 0.25 |
| 18 | 27.4390 | 3.25059 | 3025.25 | 2.86 |
| 19 | 28.1520 | 3.16986 | 213.37 | 0.20 |
| 20 | 28.5853 | 3.12279 | 3688.22 | 3.49 |
| 21 | 29.2280 | 3.05557 | 97.87 | 0.09 |
| 22 | 29.7038 | 3.00769 | 718.65 | 0.68 |
| 23 | 30.7607 | 2.90673 | 3722.08 | 3.52 |
| 24 | 31.1665 | 2.86979 | 129.87 | 0.12 |
| 25 | 31.7902 | 2.81490 | 4643.59 | 4.39 |
| 26 | 32.5821 | 2.74828 | 153.47 | 0.15 |
| 27 | 33.0752 | 2.70842 | 80.37 | 0.08 |
| 28 | 33.8062 | 2.64932 | 4202.48 | 3.98 |

TABLE 2-continued

| No. | Pos. [°2Th.] | d-spacing [A] | NET intencity [cts] | Relative intensity [%] |
|---|---|---|---|---|
| 29 | 34.7324 | 2.58075 | 12906.38 | 12.22 |
| 30 | 35.6643 | 2.51543 | 2372.75 | 2.25 |
| 31 | 36.5760 | 2.45480 | 661.96 | 0.63 |
| 32 | 37.1366 | 2.41901 | 133.10 | 0.13 |
| 33 | 37.6185 | 2.38913 | 95.30 | 0.09 |
| 34 | 38.3429 | 2.34564 | 2446.95 | 2.32 |
| 35 | 39.1926 | 2.29672 | 122.02 | 0.12 |

The crystal of the present invention can be prepared by a method comprising the following steps of:

(1) mixing acetic acid and sodium acetate in the molar ratio of from 1.5:1 to 1:2 (acetic acid:sodium acetate), (2) adding 0 to 2 wt % of water to the mixture, wherein said amount is based on the total weight of the mixture, (3) after the addition of water, heating the mixture to 130 to 250° C. to dissolve it, and (4) cooling the mixture, optionally with addition of a seed crystal after cooling.

In the above step (1), the molar ratio of acetic acid to sodium acetate (acetic acid:sodium acetate) is generally from 1.5:1 to 1:2 such as 1.5:1 to 1:1, 1.4:1 to 1:2, 1.27:1 to 1:2, 1.1:1 to 1:2, 1:1 to 1:2, 1:1 to 1:1.5. Given that the yield of crystal and the crystal size homogeneity of the resulting crystal is improved, the preferable molar ratio of acetic acid to sodium acetate (acetic acid:sodium acetate) is from 1.5:1 to 1:1.

In the above step (2), the amount of water to be added is generally 0 to 2 wt %, preferably 0 to 0.5 wt %, and more preferably 0 to 0.2 wt % based on the total weight of the mixture. In the above method, water is added to help the dissolution of the mixture of acetic acid and sodium acetate, and therefore, it is not necessarily to be added. It is preferable that water is not added to the mixture. Generally, when a molar amount of acetic acid is greater than that of sodium acetate, an amount of water to be added can be reduced.

In the above step (3), a temperature dissolving the mixture of acetic acid and sodium acetate (and, if necessary, water) is generally 130 to 250° C., preferably 150 to 200° C., and more preferably 150 to 170° C.

The above step (4) is a step for precipitating the sodium diacetate crystal from the solution comprising the dissolved acetic acid, sodium acetate and water. It may be possible to stop heating to allow cooling, or to force cooling by using a condenser, etc.

In this case, a seed crystal (seed) may be added as necessary after cooling. Although an amount of the seed crystal to be added is not specifically restricted, it is added in an amount at generally 0.1 to 10 wt %, preferably 0.5 to 5 wt %, and more preferably 0.9 to 1.1 wt % based on the total weight of the mixture of acetic acid and sodium acetate. Generally, if a seed crystal is added, then the resulting crystal size is large.

Although the cooling period is not specifically restricted, the size of the crystal of the present invention can be easily adjusted by changing the period. Generally, the longer cooling period is, the larger the resulting crystal size is. In the present disclosure, the cooling period refers to the period between the time when the heating is stopped and the time when the crystal begins to precipitate.

After the above step (4), the resulting crystal may be heated, generally at 40 to 80° C., and preferably at 50 to 60° C., to remove an excess of acetic acid. In this case, it is preferred that the heating is continued until pH reaches to 4.5 to 4.8.

For example, the crystal of the present invention can be prepared as follows. First, acetic acid and sodium acetate (from 1.5:1 to 1:2), and water in an amount of 0 to 2 wt % of the total weight are placed into a four-necked flask equipped with a condenser tube, and the mixture is agitated with a mixer. Then, the temperature is raised to from 150 to 170° C., and when almost all of the crystals of sodium acetate are dissolved, the mixture is maintained for a certain period (about 10 min.) at the temperature. Then, as necessary, the mixture is cooled, and 1 wt % of seed crystal based on the weight of the mixture of acetic acid and sodium acetate is added thereto. After crystals are precipitated, allowing the temperature to return to room temperature (about 1 to 30° C.), and removing the excess of acetic acid by using a drier at 40 to 80° C., if necessary.

The above crystal has high stability against heat or air, etc. with the suppressed volatilization of acetic acid, and therefore, it is favorable to use in solid dialysis preparations. The solid dialysis preparations comprising the crystal of the present invention are stable, because an acetic acid odor is reduced, and the acetic acid volatilization and the glucose decomposition by the acetic acid are suppressed in the preparations.

The solid dialysis preparation of the present invention comprises said crystal. As such solid dialysis preparation, no specific restriction is imposed as long as it can comprises sodium diacetate, and includes, for example, the solid dialysis preparations disclosed in JP 3433979 B, JP 10-259133 A and JP 11-114054 A, etc.

In addition, by using said crystal, a low acetate concentration solid dialysis preparation with the reduced acetic acid odor may also be prepared. The low acetate concentration solid dialysis preparation of the present invention refers to a dialysate, wherein the concentration of acetic acid in a dialysate is not more than 5 mEq/L and preferably not more than 4 mEq/L.

Preferably, the solid dialysis preparation of the present invention comprises said sodium diacetate crystal as a pH adjuster in an A agent, for example, an A agent comprising electrolyte components such as sodium chloride, potassium chloride, calcium chloride and magnesium chloride, glucose, and said sodium diacetate crystal as a pH adjuster can be mentioned. In this case, the amount of the respective components contained in an A agent are generally within the range of sodium chloride 75 to 85 wt %, potassium chloride 1 to 3 wt %, calcium chloride 2 to 4 wt %, magnesium chloride 1 to 2 wt %, glucose 10 to 20 wt %, the sodium diacetate crystal 1 to 8 wt % and sodium acetate 0 to 5 wt %, and, as expressed by mEq/L units, $Na^+$ is in the range of 132 to 140, $K^+$ is 2.0 to 2.5, $Ca^{2+}$ is 2.5 to 3.5, $Mg^{2+}$ is 1.0 to 1.5, $Cl^-$ is 105 to 110 and $CH_3COO^-$ is 2 to 12 and glucose is 0.5 to 2.5 g/L.

In the case of the low acetate concentration dialysate, the concentration of acetic acid should be not more than 5 mEq/L (preferably not more than 4 mEq/L).

Although said A agent can be prepared by using any conventional method, for example, a method disclosed in. JP 3433979 B, JP 10-259133 A or JP 11-114054, preferably, it is prepared by using a method disclosed below.

In addition, the present invention provides a method for preparing a solid dialysis preparation, wherein a suspension of potassium chloride (and sodium acetate) is used as a binder (binding agent). That is, the method of the present invention includes the following steps as shown in the preparation flowchart in FIG. 6:

(1) preparing a mixture of sodium chloride, potassium chloride, calcium chloride and magnesium chloride, (2) adding a solution of potassium chloride and water or a solution or suspension of potassium chloride, sodium acetate and water to the mixture to granulate it, and (3) drying the resulting granules.

In the above step (1), the respective components are mixed to obtain, preferably, 75 to 90 wt % of sodium chloride, 0.5 to 2.5 wt % of potassium chloride, 2.0 to 5.0 wt % of calcium chloride and 1.0 to 3.0 wt % of magnesium chloride.

In the above step (2), preferably, the amount ranges of the respective components contained in the solution or suspension to be used are 0.5 to 2.5 wt % of potassium chloride and 0 to 6 wt % of sodium acetate. In addition, water to be used is not specifically restricted, however, generally, purified water.

When preparing the above solution or suspension, it is preferred to dissolve potassium chloride and sodium acetate by heating at generally 50 to 150° C. and preferably 80 to 100° C.

In the above step (3), it may be preferred to dry under the condition of 80 to 150° C. for 30 to 120 min.

Additionally, in the above method, by using the crystal of the present invention, the volatilization of acetic acid and the decomposition of glucose are suppressed, and the solid dialysis preparation, which is stable and has a superior content uniformity, may be obtained (See preparation flow-chart in FIG. 7).

Therefore, the method for preparing the solid dialysis preparation of the present invention includes the following steps:

(1) preparing a mixture of sodium chloride, potassium chloride, calcium chloride and magnesium chloride, (2) adding a solution of potassium chloride and water or a solution or suspension of potassium chloride, sodium acetate and water to the mixture to granulate it, (3) drying the resulting granules, and (4) adding glucose and sodium diacetate crystal to the granules to mix them.

In the above step (1), the respective components are mixed to obtain, preferably, 75 to 90 wt % of sodium chloride, 0.5 to 2.5 wt % of potassium chloride, 2.0 to 5.0 wt % of calcium chloride and 1.0 to 3.0 wt % of magnesium chloride.

In the above step (2), preferably, the amount ranges of the respective components contained in the solution or suspension to be used are 0.5 to 2.5 wt % of potassium chloride and 0 to 6.0 wt % of sodium acetate. In addition, water to be used is not specifically restricted, however, generally, purified water.

When preparing the above solution or suspension, it is preferred dissolving potassium chloride and sodium acetate by heating at generally 50 to 150° C. and preferably 80 to 100° C.

In the above step (3), it is preferred to dry under the condition of 80 to 150° C. for 30 to 120 min.

In the above step (4), the sodium diacetate crystal and glucose are added to the mixture in an amount ranging from 1.0 to 8.0 wt % and 10 to 20 wt %, respectively, based on the total weight of the mixture.

An A agent obtainable as described above can be used with a B agent for preparing a dialysate by dissolving and diluting the respective agents with water and mixing them before use. As for a B agent, any conventional components such as sodium bicarbonate can be used.

Further, the present invention provides use of said crystal for preparing said solid dialysis preparation (especially A agent).

In addition, the present invention provides use of said crystal or said solid dialysis preparation (especially A agent) for preparing a dialysate.

Furthermore, the present invention provides a method for dialysis by using the dialysate prepared by using said crystal or said solid dialysis preparation (especially A agent). For example, a dialysate is prepared by dissolving and diluting said A agent and B agent (any components conventionally known in the art such as sodium bicarbonate) respectively with water and mixing them before use, and the dialysis can be done by employing said dialysate. Subjects (patients) and target diseases for said dialysis method include those conventionally known in the art.

Examples

Now, the specific embodiments of the present invention are explained by way of the following Examples, however, it should be understood that the technical scope of the present invention is not restricted to those Examples.

In Examples, solution H-NMR, solid $C^{13}$-NMR, IR (microscopic ATR method and micro-transmission method), powder X-ray diffraction and crystal size were determined by using following methods:

(1) Solution H-NMR

500 MHz NMR system (Agilent Technologies Inc.) employing an indirect detection liquid NMR probe was used under the following conditions for determination.

Analytical conditions:
Relaxation delay: 1.5 sec
Pulse degrees: 45.0°
Acquisition time: 3.5 sec
Repetitions: 32

(2) Solid $C^{13}$-NMR

600 MHz NMR system (Agilent Technologies Inc.) employing 3.2 mm HXY MAS solid NMR probe is used under the following conditions for determination.

Analysis conditions:
Contact time: 10 ms
Acquisition time: 100 ms
Recycle delay: 1 min
Total scan: 16

(3) IR (i) Microscopic ATR method
Performed by using ATR PRO450-S and FT/IR-6100 (JASCO Corporation).

(ii) Micro-transmission method
Performed by using IRT-5000 and FT/IR-6100 (JASCO Corporation).

(4) Powder X-ray diffraction
X-ray diffractometer: X's Pert PRO MPD (Spectris Co., Ltd.)
Target: Cu
X-ray tube current: 40 mV
X-ray tube voltage: 45 kV
Scan range: 2θ=4.0 to 40.0°
Pretreatment: Grinding by using an agate mortar.

(5) Crystal size (median size ($D_{50}$))
Determined in compliance with the agitation method described in the analytical sieving of the section of Particle Size Determination in the Japanese Pharmacopoeia.

Specifically, sieves were stacked on top of one another in ascending order of sieve mesh, and then a test powder was placed on the top sieve. After agitating the sieves, the weight of the sample retained on each sieve was determined to give the reference weight percentage of powder (%). A sonic sieving particle size analyzer robot sifter (RPS-105M; Seishin Enterprise Co., Ltd.) was used as the measurement device, and the sieves of the Japanese Industrial Standards were used (mesh sizes 2 mm, 1.4 mm, 1 mm, 850 μm, 600 μm, 500 μm, 425 μm, 355 μm, 300 μm, 250 μm, 150 μm and 106 μm).

In addition, a particle size corresponding to the median of the particle size distribution (median size ($D_{50}$)) was calculated by using following equation, with the results shown in FIG. 8.

$$Z = \log X_{j+1} + (\log X_j - \log X_{j+1}) \times (Q_{50} - Q_{j+1})/(Q_j - Q_{j+1})$$

$$D_{50} = 10^Z$$

$D_{50}$: Median size
$X_j$ and $X_{j+1}$: Arbitrary particle size
$Q_j$ and $Q_{j+1}$: Integrated % at $X_j$ and $X_{j+1}$ Example 1

To a four-necked flask (500 mL) equipped with a thermometer, a Liebig condenser and a stirrer (DM-30, AS ONE Corporation), 40 g of sodium acetate, 31 mL of acetic acid and 72 mg of water were added. The flask was placed into an oil bath filled with silicone oil (KF-96, Shin-Etsu Chemical Co., Ltd.), and heated with a hot plate (MR3001, Heidolph Instrument GmbH & Co. KG) such that the temperature in the flask reaches to 140 to 160° C., while agitating at the rotation speed of 100 to 200 rpm.

After white powders were dissolved to give a suspension, the heating was stopped when white crystals were deposited on the flask wall. Then, the rotation speed of the agitation was down to 50 rpm when the temperature in the flask started to decline. When the crystals were start precipitating, the rotation speed of the agitation was accelerated back to about 100 to 200 rpm.

The crystals were harvested when the temperature was sufficiently lowered, and an excess of acetic acid was removed by heating at 60° C. until pH reaches to 4.5 to 4.8. Yield: 98% (to the total weight) and median size ($D_{50}$): 1500 μm In addition, solution H-NMR, solid $C^{13}$-NMR, IR (microscopic ATR method and micro-transmission method) and powder X-ray diffraction were performed on the obtained crystals. The results of the determination of solution H-NMR, solid $C^{13}$-NMR and IR are shown below. Further, the obtained powder X-ray diffraction pattern is shown in above Table 1 and FIG. 1.

(1) Solution H-NMR
Peaks were detected at chemical shifts 23.66 and 179.59 ppm.
(2) Solid $C^{13}$-NMR
Peak was detected at chemical shift 1.998 ppm.
(3) IR
(i) Microscopic ATR method
Peaks were detected at 452.225, 636.394, 922.771, 1400.07 and 1698.02 $cm^{-1}$.

(ii) Micro-transmission method
Peaks were detected at 937.235, 1403.92, 1713.44 and 3425.92 $cm^{-1}$.

Comparative Example 1

As a comparative example, a commercially available sodium diacetate powder (DAITO CHEMICAL CO., LTD.; "Sanmi Ace™ 42", mean particle size: not more than 100 μm (catalog value)) was used. Under the same condition as in Example 1, solution H-NMR, solid $C^{13}$-NMR, and powder X-ray diffraction were measured. The results of the measurement of solution H-NMR and solid $C^{13}$-NMR are shown below. Also, the obtained powder X-ray diffraction pattern is shown in above Table 2 and FIG. 2.
(1) Solution H-NMR
Peaks were detected at chemical shifts 23.67 and 179.55 ppm.
(2) Solid $C^{13}$-NMR
Peak was detected at chemical shift 1.998 ppm.

Comparative Example 2

A commercially available sodium diacetate reagent (Wako Pure Chemical Industries, Ltd.) was used. IR (microscopic ATR method and micro-transmission method) of said powder was determined under the same condition as in Example 1. The results of the IR are shown below.
(1) IR
(i) Microscopic ATR method
Peaks were detected at 452.225, 636.394, 925.664, 1401.03 and 1698.02 $cm^{-1}$.
(ii) Micro-transmission method
Peaks were detected at 943.02, 1404.89, 1711.51 and 3427.85 $cm^{-1}$.

As described above, the results of solution H-NMR and solid $C^{13}$-NMR for the conventional crystal of Comparative Example 1 are similar to those of the crystal of Example 1, and the results of IR of the sodium diacetate reagent of Comparative Example 2 are similar to those of the crystal of Example 1. On the one hand, as shown in the above Table 2 and FIG. 2, the powder X-ray diffraction pattern obtained in Comparative Example 1 was different from that of the crystal of Example 1.

Test Example 1 Comparison of Crystal Form

The images of the sodium diacetate crystal obtained in Example 1 and the conventional crystal of Comparative Example 1 were captured by using the digital microscope KH-7700 (HIROX Co., Ltd.), and their crystal forms were compared (FIG. 3). As apparent from FIG. 3, the crystal of Example 1 (FIG. 3A) has a bigger crystal size than the conventional crystal of Comparative Example 1 (FIG. 3B).

Test Example 2 Comparison of Stability

The stabilities of the crystal of Example 1 and the crystal of Comparative Example 1 were compared by a pH measurement.
First, a petri dish containing both samples was dried at 110° C. in a fine oven (DF42, Yamato Scientific Co., Ltd.), and 0.5 g of each sample was dissolved in water to make 50 mL, and its pH was determined over time (0, 10, 20, 30 and 40 min). The results are shown in Table 3 and FIG. 4.

TABLE 3

| Stabilities of the samples at drying temperature of 110° C. (pH change) | | | | | |
|---|---|---|---|---|---|
| (min) | 0 | 10 | 20 | 30 | 40 |
| Com. Ex. 1 | 4.64 | 4.66 | 4.81 | 4.82 | 4.87 |
| Ex. 1 | 4.54 | 4.63 | 4.76 | 4.74 | 4.76 |

The pH stabilities at the drying temperature of 110° C. show that Comparative Example 1 was unstable after 20 min, while Example 1 was stable. It is thought that, after 20 min., less acetic acid was volatilized from the crystal of the present invention, and therefore, the increase of pH was suppressed. Accordingly, it is expected that Example 1 is more stable than Comparative Example 1. Comparative Example 1 is in a form of fine powder, while Example 1 has a cubic-like crystalline structure, and it is thus believed that this difference of crystalline structures contributes to the stability.

Example 2

To a four-necked flask (500 mL) equipped with a thermometer, a Liebig condenser and a stirrer (DM-30, AS ONE Corporation), 60 g of sodium acetate and 53.1 mL of acetic acid were added. The temperature of an oil bath (OB-200AM, AS ONE Corporation) filled with silicone oil (KF-96, Shin-Etsu Chemical Co., Ltd.) was set to 180° C., while agitating at the rotation speed of 150 to 200 rpm, and heating the flask such that the temperature inside the flask reaches to 150 to 160° C.

After white powders were dissolved to give a liquid, the oil bath was cooled to allow the temperature inside of the flask to become 120 to 150° C. Once the temperature was stabilized, seed crystals (150 to 500 μm, 1.2 g) were added to the flask. Then, the rotation speed of the agitation was lowered to 110 to 160 rpm, allowing the crystals to precipitate.

Then, the crystals were harvested and allowed to reach the room temperature, and an excess of acetic acid was removed by heating at 70° C. until arriving at targeted pH (4.5 to 4.8).

Example 3

To a four-necked flask (500 mL) equipped with a thermometer, a Liebig condenser and a stirrer (DM-30, AS ONE Corporation), 60 g of sodium acetate and 58.6 mL of acetic acid were added. The temperature of an oil bath (OB-200AM, AS ONE Corporation) filled with silicone oil (KF-96, Shin-Etsu Chemical Co., Ltd.) was set to 180° C., while agitating at the rotation speed of 170 to 180 rpm, and heating the flask such that the temperature inside the flask reaches to 150 to 160° C.

After white powders were dissolved to give a liquid, the oil bath was cooled to allow the temperature inside the flask to become 120 to 150° C. Once the temperature was stabilized, seed crystals (150 to 500 μm, 1.2 g) were added to the flask. Then, the rotation speed of the agitation was lowered to 120 to 165 rpm, allowing the crystals to precipitate.

Then, the crystals were harvested and allowed to reach the room temperature, and an excess of acetic acid was removed by heating at 70° C. until arriving at targeted pH (4.5 to 4.8).

Example 4

To a four-necked flask (500 mL) equipped with a thermometer, a Liebig condenser and a stirrer (DM-30, AS ONE Corporation), 60 g of sodium acetate and 41.8 mL of acetic acid were added. The temperature of an oil bath (OB-200AM, AS ONE Corporation) filled with silicone oil (KF-96, Shin-Etsu Chemical Co., Ltd.) was set to 180° C., while agitating at the rotation speed of 200 rpm, and heating the flask such that the temperature inside the flask reaches to 150 to 160° C.

After white powders were dissolved to give a liquid, the oil bath was cooled to allow the temperature inside the flask to become 120 to 150° C. Once the temperature was stabilized, seed crystals (not more than 150 μm, 1.0 g) were added to the flask. Then, the rotation speed of the agitation was lowered to 150 rpm, allowing the crystals to precipitate.

Then, the crystals were harvested and allowed to reach the room temperature, and an excess of acetic acid was removed by heating at 75° C. until arriving at targeted pH (4.5 to 4.8).

Example 5

To a four-necked flask (500 mL) equipped with a thermometer, a Liebig condenser and a stirrer (DM-30, AS ONE Corporation), 60 g of sodium acetate, 46.0 mL of acetic acid and 2.17 mL of water were added. The temperature of an oil bath (OB-200AM, AS ONE Corporation) was set to 180° C., while agitating at the rotation speed of 50 to 110 rpm, and heating the flask such that the temperature inside the flask reaches to 150 to 160° C.

After white powders were dissolved to give a liquid, the crystals were precipitate by cooling slowly.

Then, the crystals were harvested and allowed to reach the room temperature, and an excess of acetic acid was removed by heating at 70° C. until arriving at targeted pH (4.5 to 4.8).

Test Example 3

Following the above described methods for determining crystal size (median size ($D_{50}$)), the particle size distribution and the median size (median size ($D_{50}$)) of the crystals obtained in Comparative Examples 1 and 2 and Examples 2 to 5 were determined for comparison. The results are shown in Table 4.

TABLE 4

| | (%) | | | | | |
|---|---|---|---|---|---|---|
| Mesh (μm) | Com. Ex.1 | Com. Ex.2 | Ex. 2 | Ex.3 | Ex. 4 | Ex.5 |
| pass | 41.76 | 16.33 | 0.00 | 1.74 | 0.07 | 1.47 |
| 106 | 52.53 | 63.67 | 0.00 | 0.13 | 0.06 | 1.01 |
| 150 | 5.08 | 15.92 | 0.14 | 0.23 | 1.65 | 9.71 |
| 250 | 0.25 | 0.41 | 0.19 | 0.10 | 2.79 | 7.79 |
| 300 | 0.00 | 1.23 | 0.48 | 0.41 | 6.59 | 15.48 |
| 355 | 0.13 | 0.40 | 0.79 | 0.67 | 8.30 | 17.60 |
| 425 | 0.00 | 0.41 | 1.39 | 1.15 | 10.46 | 17.04 |
| 500 | 0.13 | 0.21 | 2.27 | 1.97 | 10.96 | 13.19 |
| 600 | 0.12 | 1.42 | 12.13 | 12.15 | 26.23 | 11.72 |
| 850 | — | — | 11.62 | 9.89 | 9.69 | 1.68 |
| 1000 | — | — | 29.50 | 38.61 | 14.96 | 1.96 |
| 1400 | — | — | 18.27 | 20.68 | 8.10 | 1.16 |
| 2000 | — | — | 23.21 | 12.28 | 0.14 | 0.19 |
| $D_{50}$ | 112.8 μm | 129.2 μm | 954.1 μm | 930.8 μm | 532.7 μm | 344.8 μm |

As apparent from the results of the particle size distributions and median sizes shown in Table 4 above, the crystals of the present invention have bigger crystal sizes than those of the conventional crystals.

Test Example 4 Comparison of Stability

The stabilities of the crystals obtained in Examples 2 and 3 and the crystal of Comparative Example 1 were compared by a pH measurement.

First, a petri dish containing all samples was dried at 110° C. in a fine oven (DF42, Yamato Scientific Co., Ltd.), and 0.5 g of each sample was dissolved in water to make 50 mL, and its pH was determined over time (0, 10, 20, 30, 40, 50 and 60 min). The results are shown in Table 5 and FIG. 5.

TABLE 5

Stabilities of the samples at drying temperature of 110° C. (pH change)

| | Temp. | 0 | 10 | 20 | 30 | 40 | 50 | 60 |
|---|---|---|---|---|---|---|---|---|
| Com. Ex. 1 | 110° C. | 4.66 | 4.71 | 4.79 | 4.90 | 4.85 | 5.49 | 7.02 |
| Ex. 2 | | 4.67 | 4.69 | 4.72 | 4.79 | 4.78 | 4.93 | 5.23 |
| Ex. 3 | | 4.65 | 4.67 | 4.68 | 4.75 | 4.80 | 4.92 | 5.19 |

The pH stabilities at the drying temperature of 110° C. show that Comparative Example 1 was unstable after 40 min, while Examples 2 and 3 were stable. It is thought that, after 40 min., less acetic acid was volatilized from the crystals of the present invention, and therefore, the increase of pH was suppressed. Accordingly, it is expected that Examples 2 and 3 is more stable than Comparative Example 1. Comparative Example 1 is in a form of fine powder, while Examples 2 and 3 have a cubic-like crystalline structure, and it is thus believed that this difference of crystalline structures contributes to the stability.

Example 6 Preparation of a Agent for Dialysis

Into a high-speed mixer (Model number: LFS-GS-2J, Fukae Powtec Co. Ltd.), 602.88 g of sodium chloride, 8.40 g of potassium chloride, 21.60 g of calcium chloride and 11.60 g of magnesium chloride were placed and mixed preliminary (agitator rotation speed: 230 rpm, chopper rotation speed: 350 rpm and jacket temperature: 55° C.). A suspension of potassium chloride prepared by heating 6.496 g of potassium chloride and 13.256 g of purified water in a water bath at about 90° C. to dissolve potassium chloride was added to the mixture as a binder, followed by mixing and granulation. After the addition of the binder and the granulation of the mixture, the granules were dried under the condition of 120° C. for 2 hr, and the dried materials were filled in aluminum pouches and then naturally cooled.

To 46.73 g of the obtained granules consisting of sodium chloride, potassium chloride, calcium chloride and magnesium chloride (A1 agent), 10.50 g of glucose and 2.00 g of sodium diacetate crystal were added, and after mixing, they were dispensed in packaging containers for storage to give an A agent. The formulation of the resulting A agent is as shown in Table 6 below.

TABLE 6

Formulation of the resulting Component A (Unit: mEq/L)

| Na+ | K+ | Mg²⁺ | Ca²⁺ | Glucose (mg/dL) | Sodium diacetate (as CH₃COO⁻) |
|---|---|---|---|---|---|
| 140 | 2.0 | 1.0 | 2.75 | 150 | 4.0 |

Example 7 Preparation of A1 Agent for Dialysis

Into a high-speed mixer (LFS-GS-2J, Fukae Powtec Co. Ltd.), 602.88 g of sodium chloride, 8.40 g of potassium chloride, 21.60 g of calcium chloride and 11.60 g of magnesium chloride were placed and mixed preliminary (agitator rotation speed: 230 rpm, chopper rotation speed: 350 rpm and jacket temperature: 55° C.). A suspension of potassium chloride and sodium acetate prepared by heating 6.496 g of potassium chloride, 7.93 g of sodium acetate and 13.256 g of purified water in a water bath at about 90° C. to dissolve potassium chloride and sodium acetate was added to the mixture as a binder, and mixing them before granulation. After the addition of the binder (binding agent) and the granulation of the mixture, it was dried under the condition of 120° C. for 2 hr, the dried materials were filled in aluminum pouches and then naturally cooled to give A1 agent consisting of sodium chloride, potassium chloride, calcium chloride, magnesium chloride and sodium acetate.

Comparative Example 3 Preparation of A1 Agent for Dialysis

Firstly, 602.88 g of sodium chloride, 7.936 g of potassium chloride and 19.565 g of calcium chloride were preliminary mixed together by using same condition as in Example 7. Then, 6.496 g of potassium chloride, 10.04 g of magnesium chloride, 7.93 g of sodium acetate and 13.256 g of purified water were heated in a water bath to about 90° C., and a suspension in which potassium chloride and sodium acetate were dissolved was added to the mixture as a binder (binding agent), followed by mixing and granulation. After the addition of the binder and the granulation of the mixture, the granules were dried and cooled under the condition identical to that of Example 7 to give an A1 agent consisting of sodium chloride, potassium chloride, calcium chloride, magnesium chloride and sodium acetate.

Test Example 5 Comparison of Content Uniformities in the Respective A1 Agents Firstly, 46.73 g of each A1 agent for dialysis obtained in Example 7 and Comparative Example 3 were precisely adjusted to 200 mL with purified water, and the solutions were diluted by 133-times. For these samples, every kind of cations was quantitated by using a high-performance liquid chromatography (HPLC) and the segregation was confirmed. HPLC analytical conditions are as described below. The results are shown in Table 7.

[Analytical Conditions for HPLC]

Instrument: High-performance liquid chromatograph (LC-20AD, Shimadzu Corporation)

Column: IC YS-50 (DKK-TOA CORPORATION)

Column temperature: 40° C.

Sample volume: 10 μL

Mobile phase: 5 mM methanesulfonic acid, 1 mM 18-crown-6

Flow rate: 0.5 mL/min

In Table 7 below, quantitative values of every kind of cations are shown as % relative to theoretical values.

TABLE 7

Quantitative values of cations (% to theoretical values)

|  | Na | K | Ca | Mg |
|---|---|---|---|---|
| Ex. 7 | 98.3 | 99.8 | 101.3 | 97.7 |
| Com. Ex. 3 | 98.4 | 95.2 | 80.3 | 87.2 |

As shown in Table 7, it is apparent that is the formulation of Example 7 has a composition very close to the respective theoretical values compared to that of Comparative Example 3, therefore, which is superior in the content uniformity.

Test Example 6 Determination of the Amounts of Glucose Degradation Product (Amount of 5-HMF) and Acetic Acid According to Example 6, 59.23 g of each A agent were prepared by using the sodium diacetate crystal obtained in Example 1, the conventional crystal of Comparative Example 1 or the sodium diacetate reagent of Comparative Example 2, and then were filled into each storage bag (made of polyethylene) for Kindaly 4E (Fuso Pharmaceutical Industries, Ltd.). These were storage under the condition of 40±1° C. and 75±5% RH for 4 weeks, and the amounts of 5-HMF and acetic acid were determined at the beginning and the end of this 4-week period.

(1) Measurement of 5-HMF

Firstly, 59.23 g of each A agent were weighed and dissolved into water to be precisely 200 mL. For each solution, an absorbance at the wave-length 284 nm was measured at the beginning and the end of the 4-week test period by using a ultraviolet-visible absorbance determination method employing a recording spectrophotometer (UV-2400PC, Shimadzu Corporation). The results are shown in below Table 8.

TABLE 8

Amounts of 5-HMF (absorbance)

|  | Ex. 1 | Com. Ex. 1 | Com. Ex. 2 |
|---|---|---|---|
| Beggining | 0.022 | 0.022 | 0.019 |
| 4-week after | 0.035 | 0.064 | 0.076 |

As shown in the above Table 8, the 5-HMF of A agent with the crystal of Example 1 after the 4-week period is about a half of the values of A agents with Comparative Example 1 and Comparative Example 2. It is therefore found that the decomposition of glucose is suppressed.

(2) Quantification of the Amount of Acetic Acid

Firstly, 59.23 g of each A agent was weighed and dissolved into water to be precisely 200 mL. Each solution was diluted by 40-times and then the amount of acetic acid was quantitated by using a high-performance liquid chromatography (HPLC). HPLC analytical conditions are as described below. The results are shown in Table 9.

[Analytical Conditions of HPLC]
Instrument: high-performance liquid chromatograph system (LC-10Avp, Shimadzu Corporation)
Column: PCI-305S (Shodex)
Column temperature: 40° C.
Sample volume: 10 μL
Mobile phase: To 1.7 mL of perchloric acid (60%), water is added to 1000 mL.
Flow rate: 0.97 mL/min

TABLE 9

Quantitated amount of acetic acid (%)

|  | Ex. 1 | Com. Ex. 1 | Com. Ex. 2 |
|---|---|---|---|
| Beggining | 102.1 | 98.9 | 96.3 |
| Minimum value | 97.0 | 90.9 | 87.6 |

As shown in the above Table 9, the reduction of acetic acid in the A agent with the crystal of Example 1 is less than that of the A agents with Comparative Examples 1 and 2. It is therefore found that the volatilization of acetic acid is suppressed.

As described above, the dialysates using the crystal of the present invention are more stable than that using the conventional crystals, because the decomposition of glucose and the volatilization of acetic acid in the former are more suppressed than those in the latter.

The invention claimed is:

1. A solid dialysis preparation comprising: a crystal of sodium diacetate, which has a median size from 300 to 3000 μm, and has a powder X-ray diffraction pattern having peaks at each of 11.16, 13.65, 15.77, 19.33, 20.19, 20.90, 21.66, 22.38, 23.73, 25.04, 26.28, 27.47, 28.61, 29.80, 30.78, 31.82, 33.83, 34.76, 35.69, 36.60, 38.38 and 39.22° (respectively ±0.2°) within the scanning range of the diffraction angle 2θ from 4.0 to 40.0°, and
an electrolyte.

2. A method for preparing a solid dialysis preparation comprising the steps of:
(1) preparing a mixture of sodium chloride, potassium chloride, calcium chloride and magnesium chloride,
(2) adding a solution of potassium chloride and water or a solution or suspension of potassium chloride, sodium acetate and water to the mixture to granulate it,
(3) drying the resulting granules, and
(4) adding glucose and sodium diacetate crystal to the granules to mix them, wherein the sodium diacetate crystal has a median size from 300 to 3000 μm, and has a powder X-ray diffraction pattern having peaks at each of 11.16, 13.65, 15.77, 19.33, 20.19, 20.90, 21.66, 22.38, 23.73, 25.04, 26.28, 27.47, 28.61, 29.80, 30.78, 31.82, 33.83, 34.76, 35.69, 36.60, 38.38 and 39.22° (respectively ±0.2°) within the scanning range of the diffraction angle 2θ from 4.0 to 40.0°.

3. A method for preparing a solid dialysis preparation comprising the steps of:
(1) preparing a mixture of sodium chloride, potassium chloride, calcium chloride and magnesium chloride,
(2) adding a solution of potassium chloride and water or a solution or suspension of potassium chloride, sodium acetate and water to the mixture to granulate it,
(3) drying the resulting granules, and
(4) adding glucose and sodium diacetate crystal to the granules to mix them, wherein the sodium diacetate crystal having a powder X-ray diffraction pattern as set forth in Table 1 below.

TABLE 1

| No. | Pos [°2Th] | d-spacing [A] | NET intencity [cts] | Relative intensity [%] |
|---|---|---|---|---|
| 1 | 11.1605 | 7.92820 | 26758.21 | 33.09 |
| 2 | 13.6518 | 6.48649 | 20925.54 | 25.88 |
| 3 | 15.7738 | 5.61832 | 644.63 | 0.80 |
| 4 | 19.3315 | 4.59165 | 5340.13 | 6.60 |

TABLE 1-continued

| No. | Pos [°2Th] | d-spacing [A] | NET intencity [cts] | Relative intensity [%] |
|---|---|---|---|---|
| 5 | 20.1948 | 4.39727 | 274.54 | 0.34 |
| 6 | 20.8996 | 4.25054 | 12043.18 | 14.89 |
| 7 | 21.6592 | 4.10315 | 383.97 | 0.47 |
| 8 | 22.3778 | 3.97300 | 80869.79 | 100.00 |
| 9 | 23.7331 | 3.74910 | 3783.16 | 4.68 |
| 10 | 25.0379 | 3.55659 | 11303.30 | 13.98 |
| 11 | 26.2780 | 3.39151 | 6553.25 | 8.10 |
| 12 | 27.4715 | 3.24682 | 3024.57 | 3.74 |
| 13 | 28.6062 | 3.12056 | 4242.16 | 5.25 |
| 14 | 29.8049 | 2.99772 | 93.49 | 0.12 |
| 15 | 30.7845 | 2.90453 | 4309.01 | 5.33 |
| 16 | 31.8208 | 2.81226 | 5006.29 | 6.19 |
| 17 | 33.8305 | 2.64747 | 3586.83 | 4.44 |
| 18 | 34.7557 | 2.57908 | 14622.64 | 18.08 |
| 19 | 35.6909 | 2.51362 | 2981.54 | 3.69 |
| 20 | 36.6025 | 2.45308 | 534.59 | 0.66 |
| 21 | 38.3763 | 2.34367 | 2938.49 | 3.63 |
| 22 | 39.2223 | 2.29505 | 182.52 | 0.23 |

4. A method for preparing a solid dialysis preparation comprising the steps of:
   (1) preparing a mixture of sodium chloride, potassium chloride, calcium chloride and magnesium chloride,
   (2) adding a solution of potassium chloride and water or a solution or suspension of potassium chloride, sodium acetate and water to the mixture to granulate it,
   (3) drying the resulting granules, and
   (4) adding glucose and sodium diacetate crystal to the granules to mix them, wherein the sodium diacetate crystal is the crystal having a powder X-ray diffraction pattern as depicted in FIG. 1.

* * * * *